US00PP22918P2

(12) United States Plant Patent
Oudshoorn

(10) Patent No.: US PP22,918 P2
(45) Date of Patent: Jul. 31, 2012

(54) ***MONARDA* PLANT NAMED 'SUGAR LACE'**

(50) Latin Name: *Monarda didyma*
Varietal Denomination: Sugar Lace

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/931,683

(22) Filed: Feb. 7, 2011

(51) Int. Cl.
*A01H 5/00* (2006.01)

(52) U.S. Cl. ..... Plt./455

(58) Field of Classification Search ..... Plt./455
See application file for complete search history.

*Primary Examiner* — Annette Para
(74) *Attorney, Agent, or Firm* — C. A. Whealy

(57) ABSTRACT

A new and distinct cultivar of *Monarda* plant named 'Sugar Lace', characterized by its compact, upright and outwardly spreading plant habit; freely branching habit; freely flowering habit; red purple-colored flowers; and relatively resistance to Powdery Mildew.

2 Drawing Sheets

Botanical designation: *Monarda didyma*.
Cultivar denomination: 'SUGAR LACE'.

BACKGROUND OF THE INVENTION

The present invention relates to a new and distinct cultivar of *Monarda* plant, botanically known as *Monarda didyma* and hereinafter referred to by the name 'Sugar Lace'.

The new *Monarda* plant is a product of a planned breeding program conducted by the Inventor in Rijpwetering, The Netherlands. The objective of the breeding program is to create new compact and freely flowering *Monarda* plants that are resistant to Powdery Mildew.

The new *Monarda* plant originated from a cross-pollination made during the summer of 2006 of *Monarda didyma* 'Pink Lace', disclosed in U.S. Plant Pat. No. 18,367, as the female, or seed, parent with *Monarda didyma* 'Pink Supreme', disclosed in U.S. Plant Pat. No. 14,204, as the male, or pollen, parent. The new *Monarda* plant was discovered and selected by the Inventor as a single flowering plant from within the progeny of the stated cross-pollination grown in a controlled environment in Rijpwetering, The Netherlands during the summer of 2007.

Asexual reproduction of the new *Monarda* plant by softwood cuttings in Rijpwetering, The Netherlands, since the summer of 2007, has shown that the unique features of this new *Monarda* plant are stable and reproduced true to type in successive generations.

SUMMARY OF THE INVENTION

Plants of the new *Monarda* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Sugar Lace'. These characteristics in combination distinguish 'Sugar Lace' as a new and distinct *Monarda* plant:

1. Compact, upright and outwardly spreading plant habit.
2. Freely branching habit.

3. Freely flowering habit.
4. Red purple-colored flowers.
5. Relatively resistant to Powdery Mildew.

Plants of the new *Monarda* differ primarily from plants of the female parent, 'Pink Lace' in the following characteristics:

1. Plants of the new *Monarda* are more compact than plants of 'Pink Lace'.
2. Flowers of plants of the new *Monarda* are darker in color than flowers of plants of 'Pink Lace'.

Plants of the new *Monarda* differ primarily from plants of the male parent, 'Pink Supreme' in the following characteristics:

1. Plants of the new *Monarda* are more compact than plants of 'Pink Supreme'.
2. Plants of the new *Monarda* are more freely flowering than plants of 'Pink Lace'.

Plants of the new *Monarda* can be compared to plants of *Monarda* 'Petite Delight', disclosed in U.S. Plant Pat. No. 10,784. In side-by-side comparisons plants of the new *Monarda* differ from plants of 'Petite Delight' in the following characteristics:

1. Plants of the new *Monarda* are more freely branching than plants of 'Petite Delight'.
2. Plants of the new *Monarda* are more freely flowering than plants of 'Petite Delight'.
3. Flowers of plants of the new *Monarda* are darker in color than flowers of plants of 'Petite Delight'.

BRIEF DESCRIPTION OF THE PHOTOGRAPHS

The accompanying colored photographs illustrate the overall appearance of the new *Monarda* plant showing the colors as true as it is reasonably possible to obtain in colored reproductions of this type. Colors in the photographs may differ slightly from the color values cited in the detailed botanical description which accurately describe the actual colors of the new *Monarda* plant.

The photograph on the first sheet is a side perspective view of a typical plant of 'Sugar Lace' grown in an outdoor nursery.

The photograph at the top of the second sheet is a close-up view of typical flowers of 'Sugar Lace'.

The photograph at the bottom of the second sheet is a close-up view of the upper surface of a typical leaf of 'Sugar Lace'.

DETAILED BOTANICAL DESCRIPTION

The aforementioned photographs and following observations, measurements and values describe plants grown during the autumn in an outdoor nursery in Hillegom, The Netherlands and under typical production conditions. During the production of the plants, day temperatures ranged from 12° C. to 26° C. and night temperatures ranged from 4° C. to 16° C. Plants were two years old when the photographs and the description were taken. In the detailed description, color references are made to The Royal Horticultural Society Colour Chart, 2007 Edition, except where general terms of ordinary dictionary significance are used.

Botanical classification: *Monarda didyma* 'Sugar Lace'.

Parentage:

*Female, or seed, parent.*—*Monarda didyma* 'Pink Lace', disclosed in U.S. Plant Pat. No. 18,367.

*Male, or pollen, parent.*—*Monarda didyma* 'Pink Supreme', disclosed in U.S. Plant Pat. No. 14,204.

Propagation:

*Type cutting*.—By softwood cuttings.

*Time to initiate roots, summer*.—About two weeks at 18° C.

*Time to produce a rooted young plant, summer*.—About three months at 18° C.

*Root description*.—Fine, fibrous; grey brown in color.

*Rooting habit*.—Freely branching; dense.

Plant description:

*Plant and growth habit*.—Perennial; compact, upright and outwardly spreading plant form; broad inverted triangle; basal branching habit; moderately vigorous growth habit.

*Plant height*.—About 44.5 cm.

*Plant width*.—About 29.7 cm.

*Lateral branch description*.—Length: About 26.5 cm. Diameter: About 2.5 mm. Internode length: About 4.2 cm. Strength: Strong. Aspect: Upright. Texture: Densely pubescent. Color: Close to 143B.

Foliage description:

*Arrangement*.—Opposite, simple.

*Length*.—About 7.5 cm.

*Width*.—About 4 cm.

*Shape*.—Ovate.

*Apex*.—Acute.

*Base*.—Rounded to truncate.

*Margin*.—Serrate.

*Texture, upper and lower surfaces*.—Slightly rugose; pubescent.

*Venation pattern*.—Pinnate.

*Color*.—Developing leaves, upper surface: Close to 137B. Developing leaves, lower surface: Close to 137C to 137D. Fully expanded leaves, upper surface: Close to 137A and N137B; venation, close to 147C to 147D. Fully expanded leaves, lower surface: Close to 147B; venation, close to 148D.

*Petiole length*.—About 1.8 cm.

*Petiole diameter*.—About 2 mm.

*Petiole color, upper surface*.—Close to 146B to 146C.

*Petiole color, lower surface*.—Close to 144B.

Flower description:

*Flower form, arrangement and flowering habit*.—Single labiate and sessile flowers arranged in terminal globular spikes; flowers face outwardly; freely flowering habit with about 200 flowers developing per inflorescence.

*Natural flowering season*.—Continuous flowering from late July to late September in The Netherlands.

*Flower longevity on the plant*.—About five days; flowers not persistent.

*Fragrance*.—Faintly fragrant; spicy, pleasant.

*Flower buds*.—Length: About 1.5 cm. Diameter: About 2.5 mm. Shape: Narrowly oblanceolate; curved. Color: Close to 68A to 68B; towards the base, close to 145C to 145D.

*Inflorescence size*.—Length: About 4.7 cm. Diameter: About 6.1 cm.

*Flowers*.—Diameter: About 3 mm. Depth (height): About 2.9 cm.

*Petals*.—Arrangement: Labiate; upper lip hooded; lower lip, a single lobe; lips fused. Length, upper and lower lips: About 2.5 cm. Width, upper lip: About 1 mm. Width, lower lip: About 4 mm. Shape, upper lip: Lanceolate; apex, narrowly acute. Shape, lower lip: Oblanceolate; apex, aristate. Margin, upper and lower lips: Entire. Texture, upper and lower surfaces: Pubescent. Color: When opening, upper and lower surfaces: Close to 63B. Fully opened, upper and lower surfaces: Close to 63B to 63C; color becoming closer to 72B to 72C with development.

*Sepals*.—Arrangement: Five in a single whorl; fused, tubular. Length: About 9 mm. Width: About 2.5 mm. Apex: Narrowly acute. Margin: Entire. Texture, upper and lower surfaces: Pubescent. Color: When opening, upper and lower surfaces: Close to 183A; towards the base, close to 145C to 145D. Fully opened, upper and lower surfaces: Close to N186D; towards the base, close to 145D.

*Reproductive organs*.—Stamens: Quantity per flower: Two. Filament length: About 1.5 cm. Filament color: Close to 68C to 68D. Anther length: About 1.5 mm. Anther shape: Narrowly elliptic. Anther color: Close to 71A. Pollen amount: Scarce. Pollen color: Close to 155A to 155B. Pistils: Quantity per flower: One. Pistil length: About 2.8 cm. Stigma shape: Cleft. Stigma color: Close to 72B. Style length: About 2.4 cm. Style color: Close to 75B to 75C. Ovary color: Light yellow green.

*Seed and fruit*.—Seed and fruit production have not been observed.

Disease/pest resistance: Plants of the new *Monarda* have been observed to be relatively resistant to Powdery Mildew. Plants of the new *Monarda* not been observed to be resistant to pests and other pathogens common to *Monarda* plants.

Garden performance: Plants of the new *Monarda* have exhibited good tolerance to rain and wind, have been observed to be hardy to USDA Zone 5 and to tolerate high temperatures of about 35° C.

It is claimed:

1. A new and distinct *Monarda* plant named 'Sugar Lace' as illustrated and described.

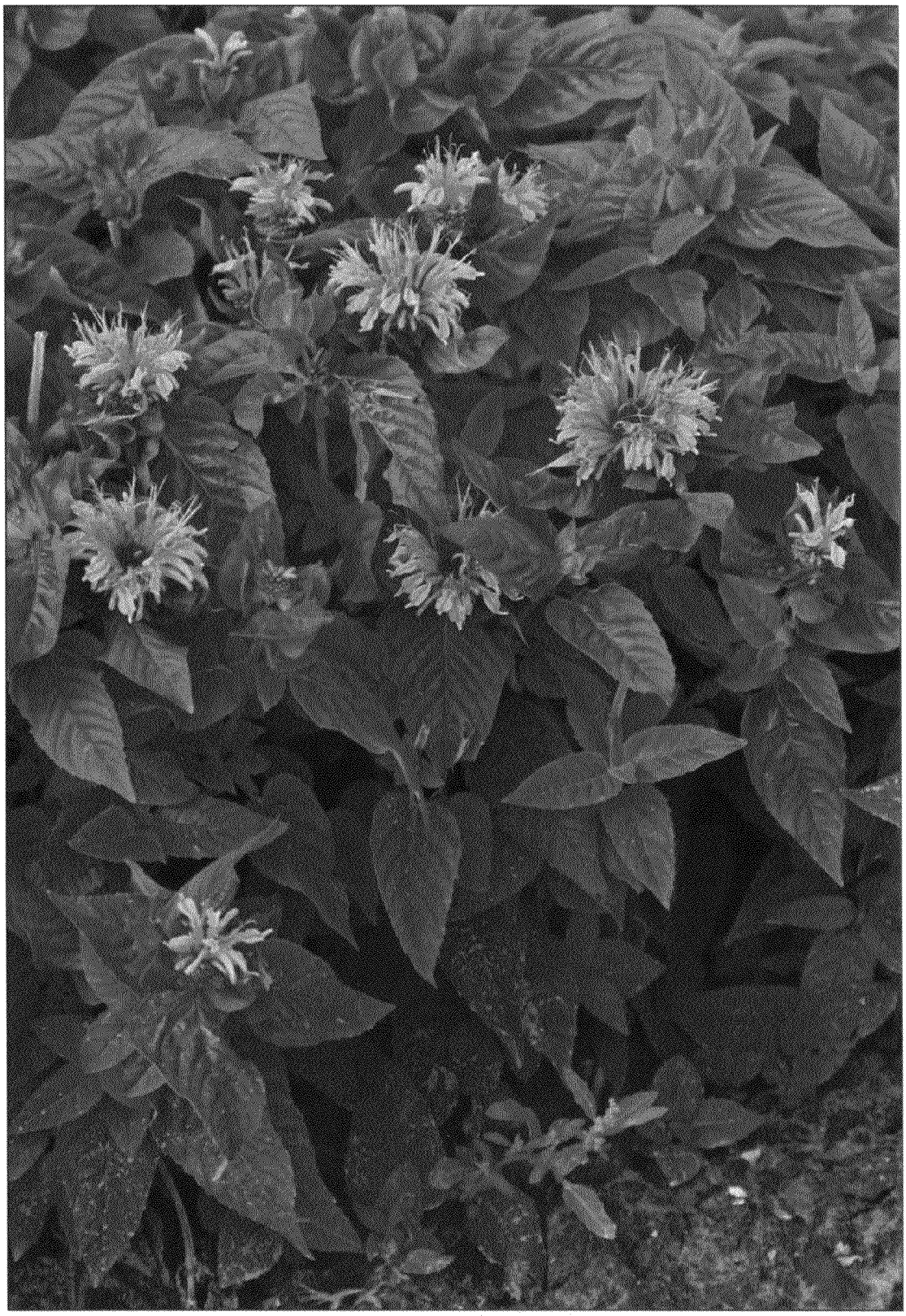

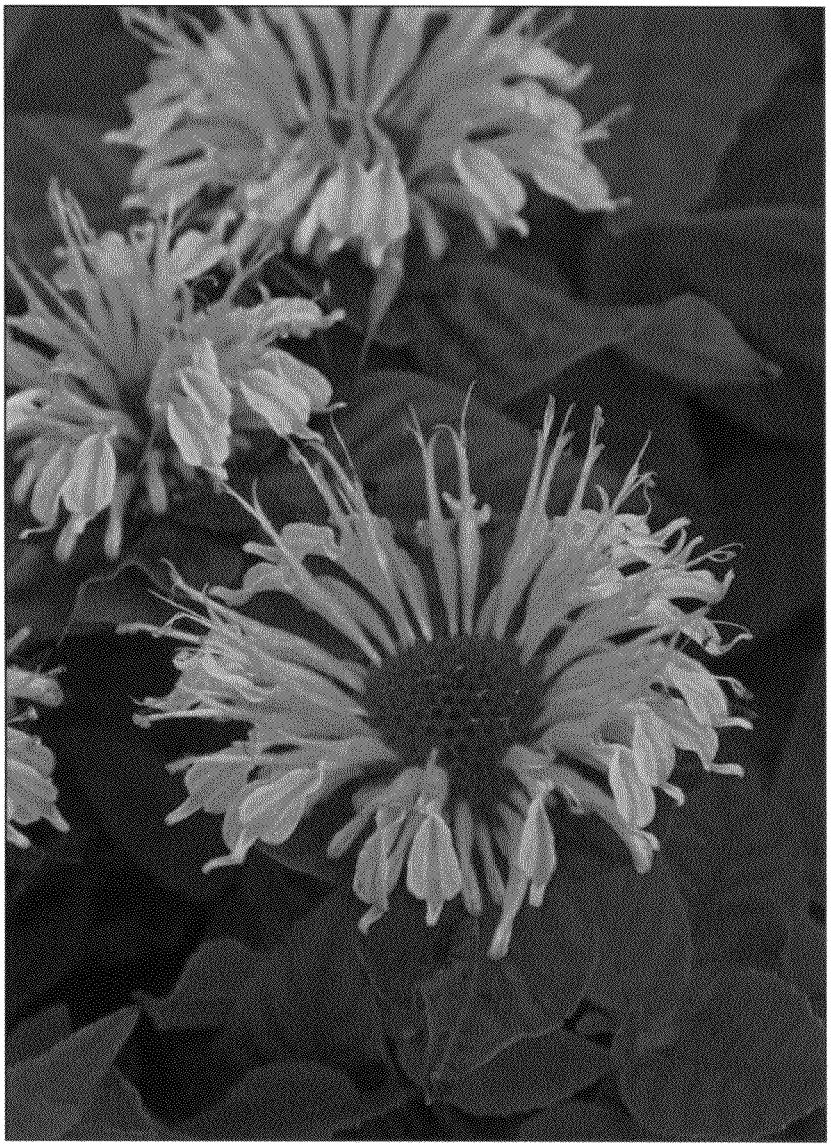
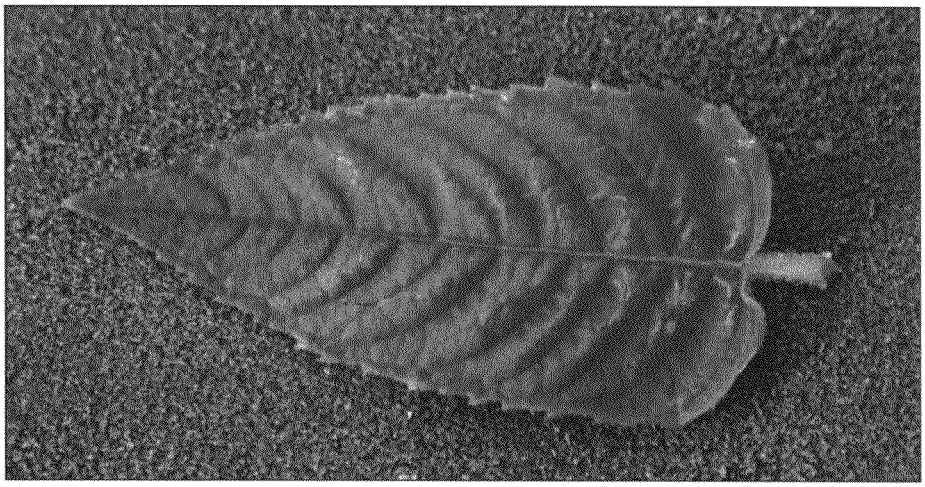

* * * * *